United States Patent
Noda et al.

(10) Patent No.: US 10,952,648 B2
(45) Date of Patent: Mar. 23, 2021

(54) MEASUREMENT DEVICE AND MEASUREMENT METHOD

(71) Applicant: NEC Solution Innovators, Ltd., Tokyo (JP)

(72) Inventors: Hisashi Noda, Tokyo (JP); Katsuyuki Nagai, Tokyo (JP); Tomomi Kinoshita, Tokyo (JP); Hiroki Terashima, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 448 days.

(21) Appl. No.: 15/580,557

(22) PCT Filed: May 12, 2016

(86) PCT No.: PCT/JP2016/064137
§ 371 (c)(1),
(2) Date: Dec. 7, 2017

(87) PCT Pub. No.: WO2016/208289
PCT Pub. Date: Dec. 29, 2016

(65) Prior Publication Data
US 2018/0168487 A1  Jun. 21, 2018

(30) Foreign Application Priority Data
Jun. 26, 2015 (JP) .............................. JP2015-129017

(51) Int. Cl.
*A61B 5/11* (2006.01)
*A61B 5/00* (2006.01)

(52) U.S. Cl.
CPC .......... *A61B 5/1128* (2013.01); *A61B 5/0077* (2013.01); *A61B 5/11* (2013.01);
(Continued)

(58) Field of Classification Search
CPC ....... A61B 5/1128; A61B 5/11; A61B 5/0077; A61B 5/112; A61B 5/1123; A61B 5/1116; A61B 5/7425; A61B 2576/00
See application file for complete search history.

(56) References Cited

U.S. PATENT DOCUMENTS

| | | | | |
|---|---|---|---|---|
| 4,631,676 A | * | 12/1986 | Pugh | A61B 5/1038 348/77 |
| 2015/0324637 A1 | | 11/2015 | Utsunomiya et al. | |
| 2015/0325004 A1 | | 11/2015 | Utsunomiya et al. | |

FOREIGN PATENT DOCUMENTS

| | | |
|---|---|---|
| JP | 2010-026235 A | 2/2010 |
| JP | 2010172394 A | 8/2010 |

(Continued)

OTHER PUBLICATIONS

Térence Coudert et al., "A method to obtain 3D foot shape deformation during the gait cycle", May 26, 2014 (May 26, 2014), XP055514487, Retrieved from the Internet: <URL:https://www.researchgate.net/publication/228912309_A_method_to_obtain_3D_foot_shape_deformation_during_the_gait_cycle>, [retrieved on Oct. 11, 2018], 5 pages total.

(Continued)

Primary Examiner — Patrick Fernandes (57) ABSTRACT

Provided is a measurement device including a first acquisition unit that acquires depth information indicating a depth for each two-dimensional position, and a measurement unit that measures a walking state of a test subject by using the depth information.

7 Claims, 9 Drawing Sheets (52) U.S. Cl.
CPC ............ *A61B 5/112* (2013.01); *A61B 5/1123* (2013.01); *A61B 5/7425* (2013.01); *A61B 2576/00* (2013.01)

(56) References Cited

FOREIGN PATENT DOCUMENTS

| JP | 2013-002884 A | 1/2013 | | |
|---|---|---|---|---|
| JP | 2015-042241 A | 3/2015 | | |
| JP | 2015062654 A | 4/2015 | | |
| WO | 2014/115817 A1 | 7/2014 | | |
| WO | WO-2014112632 A1 | * | 7/2014 | ........... A61B 5/1071 |

OTHER PUBLICATIONS

Marco Sculo, "Development of a graphical user interface for gait analysis", Sep. 23, 2011 (Sep. 23, 2011), XP055514365, Retrieved from the Internet: <URL:http://biomec.upc.edu/wp-content/uploads/2016/09/Sculto-MSc-Thesis-Development-of-a-graphical-user-interface-for-gait-analysis.pdf>, [retrieved on Oct. 11, 2018], 99 pages total.
XcitexSolutions, "Motion Analysis of Runner using ProAnalyst", Youtube, Dec. 16, 2011 (Dec. 16, 2011), pp. 1-2, XP054978775, Retrieved from the Internet: <URL:https://www.youtube.com/watch?v=TEewyWmBvvY>, [retrieved on Oct. 13, 2018], Whole video, 2 pages total.
XcitexSolutions, "3-D Motion Analysis of Robosapien using ProAnalyst", Youtube, Dec. 16, 2011 (Dec. 16, 2011), pp. 1-2, XP054978776, Retrieved from the Internet: <URL:https://www.youtube.com/watch?v=dIPggnI qLc&index=4&list=PL_-QQxXxTrVagdHCWgcvk9inJyPKJ72Wn>, [retrieved on Oct. 13, 2018], Whole video, 2 pages total.
Extended European Search Report dated Oct. 30, 2018 issued by the European Patent Office in counterpart application No. 16814060.6.
Communication dated Oct. 23, 2018, from Japanese Patent Office in counterpart application No. 2017-524727.
Hiroyuki Adachi et al., "Walking data acquisition using Kinect mounting robot," IEICE Technical Report, MICT2014-50(Oct. 2014), Oct. 2014, pp. 25-30.
International Search Report of PCT/JP2016/064137 dated Jul. 12, 2016.
Shiyang et al., "A Novel Method of Foot Detection Based on Laser Range Scanner", Computer Measurement & control, Feb. 25, 2014, vol. 22, No. 2, pp. 332-335 (total 4 pages).
Communication dated Jan. 3, 2020 from the China National Intellectual Property Administration in Application No. 201680037595.5.

* cited by examiner

MEASUREMENT DEVICE AND MEASUREMENT METHOD

CROSS REFERENCE TO RELATED APPLICATIONS

This application is a National Stage of International Application No. PCT/JP2016/064137 filed May 12, 2016, claiming priority based on Japanese Patent Application No. 2015-129017 filed Jun. 26, 2015, the contents of all of which are incorporated herein by reference in their entirety.

TECHNICAL FIELD

The present invention relates to a walking action analysis technique.

BACKGROUND ART

The analysis of a walking action has been performed in various scenes and fields. For example, a walking action is analyzed on an aged person or a patient having a problem with a motion function in order to prevent falling. In addition, also in a scene of physical therapy, walking disorder is found through the analysis of the walking action, and a method of treatment is determined.

On the other hand, there are various applications for three-dimensionally capturing the motion of a person by using a motion capture technique or a three-dimensional sensing technique and by converting the motion into digital data. A method of the motion capture includes a method of estimating the posture of a human body by using three-dimensional information obtained from a three-dimensional sensor. The three-dimensional information obtained from the three-dimensional sensor is information indicating a three-dimensional space where a test subject is actually present, and is formed on the basis of the two-dimensional information and depth information. The two-dimension indicated by the two-dimensional information is a plane of a video or an image which is obtained from a single visible light camera or the like, and a depth indicated by the depth information indicates a distance from the three-dimensional sensor which is obtained from the three-dimensional sensor, such as an infrared sensor or a plurality of visible light cameras. The three-dimensional position is determined from a two-dimensional position and a depth. According to the above-described method, it is possible to convert the motion of the human into three-dimensional data without attaching a marker or a sensor to the human body. In the estimation of the posture of the human body, portions (head, hand, arm, leg, and the like) of the limbs of the human are recognized from the three-dimensional information, and motions of the portions are recorded.

Patent Document 1 described below proposes a method of measuring walking ability by using a self-propelled device on which Kinect (registered trademark), which is a three-dimensional sensor, is mounted. In this method, the self-propelled device travels at a fixed distance from a test subject, thereby recording skeleton data (position data of a framework) obtained from Kinect (registered trademark) and converting characteristics during walking of the test subject into graphs.

RELATED DOCUMENT

Non-Patent Document

[Non-Patent Document 1] Hiroyuki Adachi, et al., "Acquisition of Walking Data Using KINECT self-propelled robot", IEICE technical report, MICT2014-50, 2014-10

SUMMARY OF THE INVENTION

Technical Problem

However, the skeleton data used in the above-proposed method has a problem in the level of accuracy. For example, although a three-dimensional position of a foot is obtained as skeleton data, a foot portion below an ankle has a certain degree of size from a heel to a toe, and thus positional information obtained as the skeleton data does not indicate the position of a fixed location with respect to the foot portion. The above-proposed method using such skeleton data has some room for an improvement in the accuracy of measurement.

The present invention is contrived in view of such situations, and an object thereof is to provide a technique for measuring a walking state with a high level of accuracy.

Solution to Problem

In aspects of the present invention, the following configurations are adopted in order to solve the above-described problems.

A first aspect relates to a measurement device. The measurement device according to the first aspect includes a first acquisition unit that acquires depth information indicating a depth for each two-dimensional position, and a measurement unit that measures a walking state of a test subject by using the depth information.

A second aspect relates to a measurement method performed by at least one computer. The measurement method according to the second aspect includes acquiring depth information indicating a depth for each two-dimensional position, and measuring a walking state of a test subject by using the depth information.

Note that, another aspect of the present invention may be a program for causing at least one computer to execute the measurement method of the second aspect, or may be a storage medium readable by a computer having the program recorded thereon. This storage medium includes a non-transitory tangible medium.

Advantageous Effects of Invention

According to the above-described aspects, it is possible to provide a technique for measuring a walking state with a high level of accuracy.

BRIEF DESCRIPTION OF THE DRAWINGS

The above-described objects, other objects, features and advantages will be further apparent from the preferred example embodiments described below, and the accompanying drawings as follows.

DESCRIPTION OF EXAMPLE EMBODIMENTS

Hereinafter, example embodiments of the invention will be described. Note that, the example embodiments described below are merely illustrative of the invention, and the invention is not limited to the configurations of the following example embodiments.

First Example Embodiment

[Configuration of Apparatus]

Figure 1:
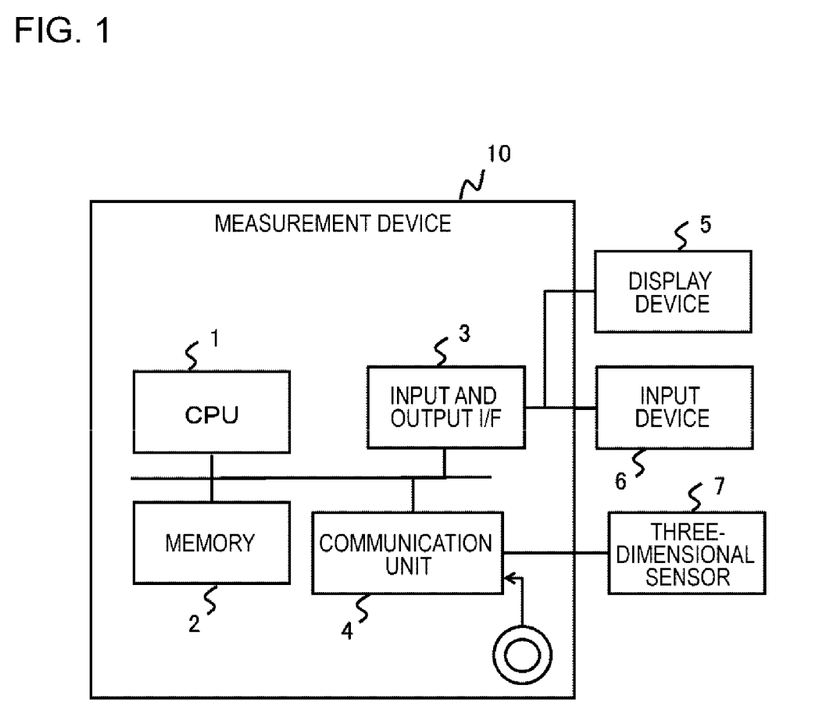
FIG. 1 is a schematic diagram illustrating an example of a hardware configuration of a measurement device according to a first example embodiment.

FIG. 1 is a schematic diagram illustrating an example of a hardware configuration of a measurement device 10 according to a first example embodiment. The measurement device 10 according to the first example embodiment is a so-called computer, and includes a Central Processing Unit (CPU) 1, a memory 2, an input and output interface (I/F) 3, a communication unit 4 and etc., which are connected to each other, for example, via a bus.

The CPU 1 includes an application-specific integrated circuit (ASIC), a Digital Signal Processor (DSP), a Graphics Processing Unit (GPU), and the like in addition to a general CPU.

The memory 2 is a Random Access Memory (RAM), a Read Only Memory (ROM), or an auxiliary storage device (hard disk or the like).

The input and output I/F 3 can be connected to user interface devices such as a display device 5 and an input device 6. The display device 5 is a device, such as a Liquid Crystal Display (LCD) or a Cathode Ray Tube (CRT) display, which displays a screen corresponding to drawing data processed by the CPU 1 and the like. The input device 6 is a device which receives an input of a user operation, such as a keyboard or a mouse. The display device 5 and the input device 6 are integrated with each other, and may be realized as a touch panel. In addition, the input device 6 may be a microphone unit that acquires a sound. Another output device such as a speaker unit may be connected to the input and output I/F 3.

The communication unit 4 performs communication with another computer through a communication network (not shown), the transmission and reception of a signal to and from another device such as a printer, or the like. The communication unit 4 is connected to a three-dimensional sensor 7 through a Universal Serial Bus (USB), or the like. However, a mode of communication between the communication unit 4 and the three-dimensional sensor 7 is not limited. In addition, a portable storage medium and the like may be connected to the communication unit 4.

The three-dimensional sensor 7 detects three-dimensional information. The three-dimensional sensor 7 is realized as a sensor in which a visible light camera and a depth sensor are integrated with each other, such as Kinect (registered trademark) or a 3D camera. The depth sensor is also referred to as a distance image sensor, and a distance between the distance image sensor and an object is calculated on the basis of information obtained by irradiating the object with a pattern of near-infrared light from a laser and capturing an image of the pattern by a camera detecting near-infrared light. The realization method of the three-dimensional sensor 7 is not limited as long as the three-dimensional sensor can detect a three-dimensional position of a predetermined portion of a test subject within a visual field. For example, the three-dimensional sensor 7 may be realized by a three-dimensional scanner system using a plurality of visible light cameras. In the following description, for convenience of description, it is assumed that the three-dimensional sensor 7 is a sensor in which a visible light camera and a depth sensor are integrated with each other.

A hardware configuration of the measurement device 10 is not limited to the example illustrated in FIG. 1. The measurement device 10 may include other hardware components not shown in the drawing. In addition, the number of hardware components is not limited to the example of FIG. 1. For example, the measurement device 10 may include a plurality of CPUs 1.

[Processing Configuration]

Figure 2:
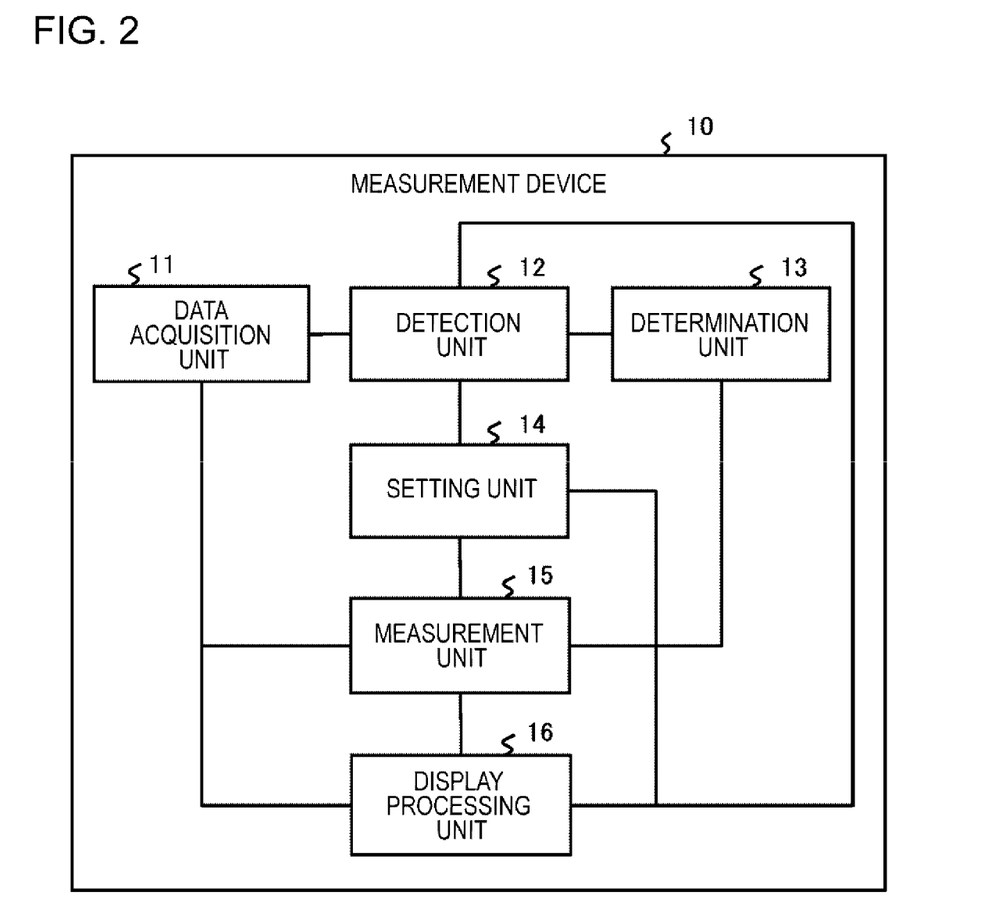
FIG. 2 is a schematic diagram illustrating an example of a processing configuration of the measurement device according to the first example embodiment.

FIG. 2 is a schematic diagram illustrating an example of a processing configuration of the measurement device 10 according to the first example embodiment. The measurement device 10 according to the first example embodiment includes a data acquisition unit 11, a detection unit 12, a determination unit 13, a setting unit 14, a measurement unit 15, a display processing unit 16, and etc. These processing modules are realized, for example, by the CPU 1 executing programs stored in the memory 2. In addition, the programs may be installed through the communication unit 4 from a portable storage medium, such as a Compact Disc (CD) or a memory card, or another computer on a network, and may be stored in the memory 2.

The data acquisition unit 11 acquires a two-dimensional image frame and a depth image (distance image) frame from the three-dimensional sensor 7 at a predetermined cycle. Both the frames may be acquired at the same cycle, or may be acquired at different cycles. Hereinafter, the frames are simply referred as a two-dimensional image and a depth image, respectively. The two-dimensional image is an image captured by the visible light camera. The depth image is data obtained by the depth sensor, and is depth information on substantially the same region as an image capture region of the two-dimensional image. The depth image indicates a depth by a value of each pixel (pixel value). That is, the depth image can also be referred to as depth information indicating a depth for each two-dimensional position. In the two-dimensional image and depth image to be acquired, coordinate systems of the respective images can be converted into each other. However, the data acquisition unit 11 can also acquire the recorded two-dimensional image and depth image from another computer or portable storage medium through the communication unit 4. In this case, the measurement device 10 may not be connected to the three-dimensional sensor 7.

In this example embodiment, the test subject is measured in a state where the side thereof faces to the three-dimensional sensor 7. Thereby, the side surface of the test subject is shown in the two-dimensional image and the depth image which are acquired by the data acquisition unit 11.

The detection unit 12 detects a foot portion of the test subject from the depth image acquired from the data acquisition unit 11. The foot portion detected here may be the entire portion below the ankle, or may be a portion including a range from the toe to the heel. For example, the detection unit 12 recognizes: the depth image which is obtained in a state where the test subject is not included, as a background image; and a set of pixels which are different from the background image, as a test subject region. The detection unit 12 detects a horizontally widest portion of the depth image at the lower end in the test subject region, as a foot portion. However, a method of detecting the foot portion by the detection unit 12 is not limited to such method. For example, the detection unit 12 may estimate the position of the foot portion of the test subject within the depth image on the basis of skeleton data (framework data) of the right foot or the left foot of the test subject which can be obtained from the acquired two-dimensional image and depth image, and detect the foot portion from a region indicating the same depth in the vicinity of the position. In this manner, it is not necessary to recognize the background image.

The determination unit 13 determines the length of the foot portion which is detected by the detection unit 12. Specifically, the determination unit 13 counts the number of pixels of a horizontally widest portion of the depth image in the foot portion which is detected by the detection unit 12. The horizontally widest portion of the depth image in the foot portion corresponds to a straight line or a region from the toe to the heel.

The setting unit 14 acquires coordinates of a scanning line in a two-dimensional coordinate system of the depth image on the basis of the position of the foot portion which is detected by the detection unit 12. The "scanning line" means a row of pixels for which depth are scanned by the measurement unit 15, within the depth image acquired by the data acquisition unit 11. The "scanning line" is conceptually equivalent to the walking surface of the test subject which is shown in the depth image. For example, the setting unit 14 handles a straight line, which is obtained by extending a line segment indicating the length of the foot portion which is determined by the determination unit 13, as a scanning line, and acquires the position of the pixel on the scanning line as coordinates of the scanning line. In this example embodiment, as described above, the test subject faces its side to the three-dimensional sensor 7, and thus the scanning line is set in the horizontal direction of the depth image. However, the scanning line which is set in the depth image may not be a straight line, and may be, for example, a curved line.

The measurement unit 15 measures a walking state of the test subject by using the depth of the coordinates (pixel) of the scanning line which is acquired by the setting unit 14. Here, in order to measure the walking state, it is significantly important to recognize a singe step with a high level of accuracy. If the position of a fixed portion within the right foot portion or left foot portion grounded can be determined every time when the foot portion is grounded to the walking surface, it is possible to recognize a single step with a high level of accuracy. On the other hand, in this example embodiment, as described above, the walking state is measured using the depth on the scanning line, and thus a processing speed is improved as compared to scanning with all of the depths.

Consequently, the measurement unit 15 determines the position of a predetermined location within the foot portion in a state where the sole of the foot of the test subject is grounded to the walking surface by using depth information on the scanning line, and the walking state of the test subject is measured using the determined position. The state where the sole of the foot of the test subject is grounded to the walking surface is equivalent to states of the foot portion of a foot flat (FF) phase and a mid-stance (MS) phase in a walking action. In a field of walking analysis, a walking action is generally classified into a heel contact (HC) phase, a FF phase, a MS phase, a heel off (HO) phase, and a toe off (TO) phase. The state where the sole of the foot of the test subject is grounded to the walking surface can be detected on the basis of a state where a line from the toe to the heel is superimposed on the scanning line. However, only with the depth on the scanning line, it is difficult to accurately detect a ground state of only the toe or the heel. This is because it is difficult to distinguish whether the portion of the foot portion which is indicated by the depth on the scanning line is the toe or the heel.

For example, the measurement unit 15 detects a state where the sole of the foot of the test subject is grounded to the walking surface as follows. The measurement unit 15 performs scanning with depth information in a predetermined direction along the scanning line to determine the position of a certain portion of the foot portion grounded to the walking surface. Specifically, the measurement unit 15 determines the position of a certain pixel having a difference in a pixel value between a pixel on the scanning line in the acquired depth image and a pixel at the corresponding position in the depth image (background image) recognized as a background by the detection unit 12. The measurement unit 15 determines whether or not the depth of the determined position of the portion equals to the depth of a position ahead of the determined position of the portion by the length of the foot portion which is determined by the determination unit 13. The measurement unit 15 can detect a state where the sole of the foot of the test subject is grounded to the walking surface in a case where both the depths equal to each other on the basis of the determination result. Here, the wording "both the depths equal to each other" may include not only a case where both the depths are completely equivalent to each other, but also a case where both the depths approximate to each other within a predetermined error. In addition, in this example embodiment, a processing load is reduced by detecting a state where the sole of the foot of the test subject is grounded to the walking surface only with the depths of two positions. However, depths of three or more positions included in a region corresponding to the length of the foot portion may be compared with each other.

Figure 3:
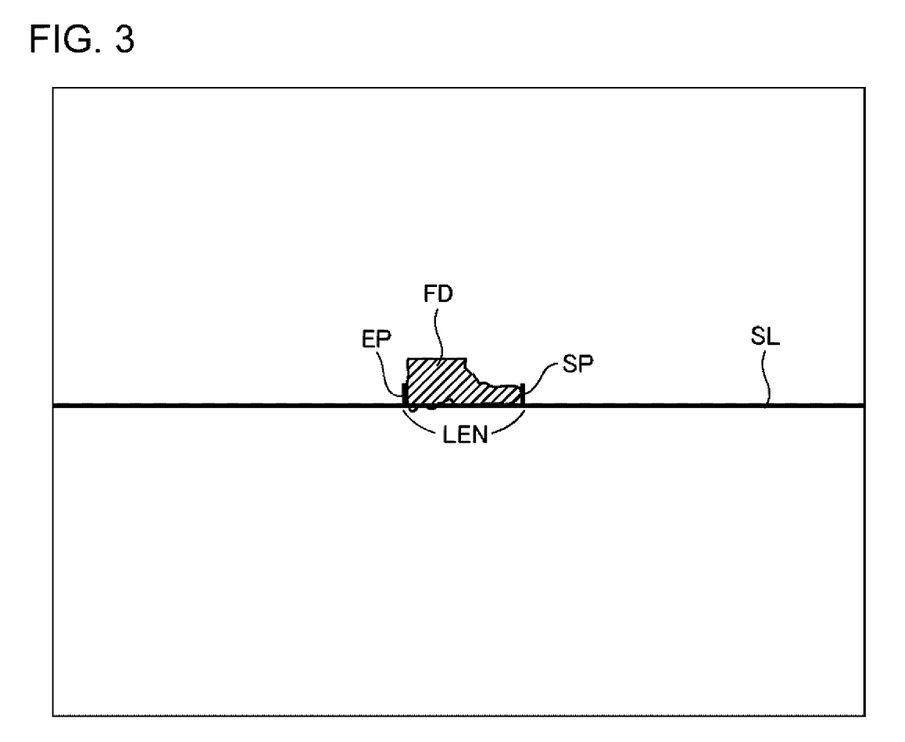
FIG. 3 is a diagram illustrating an example of a depth image indicating a foot portion in a state where the sole of the foot of a test subject is grounded to a walking surface.

FIG. 3 is a diagram illustrating an example of a depth image indicating a foot portion in a state where the sole of the foot of a test subject is grounded to a walking surface. In the example of FIG. 3, a right side surface FD of the foot portion of the test subject is shown in the depth image. In the example of FIG. 3, the measurement unit 15 performs scanning with a depth (pixel value) of a position (pixel) obtained with coordinates of a scanning line SL from the right to the left of the depth image. The measurement unit 15 firstly determines a position SP indicating a depth different from that in the background image through this scanning. In a state where the sole of the foot of the test subject is grounded to the walking surface, the position SP indicates the position of the toe as illustrated in FIG. 3. The measurement unit 15 determines a position EP ahead of the position SP by a length LEN (for example, 52 pixels) of the foot portion which is determined by the determination unit 13. In the state where the sole of the foot of the test subject is grounded to the walking surface, the position EP indicates the position of the heel. The measurement unit 15 can detect the state where the sole of the foot of the test subject is grounded to the walking surface, in a case where the depth (pixel value) of the position SP and the depth (pixel value) of the position EP equal to each other. In a state where only the heel or only the toe is grounded, that is, a state where the sole of the foot is grounded to the walking surface, these depths are different from each other.

In this example embodiment, the measurement unit 15 determines the position of the heel in the state where the sole of the foot of the test subject is grounded to the walking surface. The position of the heel is the position EP in the example of FIG. 3. However, the measurement unit 15 may determine the position of the toe, and may determine the center position between the toe and the heel.

The measurement unit 15 calculates at least one or more of an actually measured value of a step width, the number of steps, and an actually measured value of a step interval on the basis of the plurality of positions determined as described above with respect to a predetermined location (for example, the heel) within the foot portion. A real distance between adjacent positions among the plurality of positions determined is set to be the actually measured value of the step width, and the number of steps can be calculated on the basis of the number of determined positions. The step interval is an interval between the right foot and the left foot in a direction of a shoulder width (direction perpendicular to forward direction), and the actually measured value of the step interval can be calculated through comparison (difference and the like) between the depth of the foot portion one step before and the current depth of the foot portion. However, the walking state measured by the measurement unit 15 is not limited thereto. For example, the measurement unit 15 can also calculate an average step width by using an actually measured value of a step width for each step, and the degree of fluctuation (dispersion) in the step width can also be calculated. Further, the measurement unit 15 holds a time or an identification number of the frame of the depth image which is used for the determination of the positions, and thus it is possible to calculate a time difference between the determined positions. The measurement unit 15 can also calculate a walking speed by using the time difference and the actually measured value of the step width.

By the way, since positions determined with respect to the predetermined location within the foot portion indicate positions on the depth image, a distance between the positions on the depth image is not a distance in a world coordinate system, that is, the actually measured value of the step width. Accordingly, the measurement unit 15 calculates the actually measured value of the step width from the number of pixels between the positions on the depth image as follows. Specifically, the measurement unit 15 can calculate the distance (the actually measured value of the step width) between the positions in the world coordinate system by the following expression, by using the number of pixels PX1 between the determined positions, a depth DPT of the determined position, the number of pixels PX2 which is half the width (length in the horizontal direction) of the two-dimensional image, and a half (for example, 35 degrees) of a horizontal viewing angle of the three-dimensional sensor 7 (the visible light camera or the like capturing the two-dimensional image).

$$\text{Distance of World Coordinate System} = (PX1 \cdot DPT \cdot \tan 35)/PX2$$

However, a method of calculating the actually measured value of the step width is not limited to this expression. For example, PX2 may be set to be the number of pixels which is half the width (length in the horizontal direction) of the depth image, and the horizontal viewing angle may be set to be a vertical visual field angle of the depth sensor. In addition, PX1 may be set to be the number of pixels on the two-dimensional image.

The display processing unit 16 sequentially displays the two-dimensional images acquired by the data acquisition unit 11 on the display device 5. In a case where the test subject is detected in the depth image, the display processing unit 16 may determine a region indicating the test subject within the two-dimensional image and may display a two-dimensional image obtained by coloring the region of the test subject within the two-dimensional image with the depth information, on the basis of the region of the test subject which is determined within the depth image.

In addition, when coordinates of the scanning line are acquired by the setting unit 14, the display processing unit 16 can also display an image on which a linear image corresponding to the scanning line is superimposed, on the two-dimensional image acquired by the data acquisition unit 11. The position of the superimposed linear image on the two-dimensional image can be determined through conversion from the coordinate system of the depth image into the coordinate system of the two-dimensional image. The linear image superimposed and displayed on the two-dimensional image plays a role of instructing the test subject about a walking passage for measurement. That is, the test subject can easily recognize which position is good to walk by viewing the displayed linear image. The display processing unit 16 may further superimpose one or more other linear images parallel to the linear image, in addition to the linear image corresponding to the scanning line.

The display processing unit 16 can also display an image in which a mark image, which indicates the position of the predetermined location within the foot portion which is determined by the measurement unit 15, is superimposed on the two-dimensional image acquired by the data acquisition unit 11 together with the linear image. At this time, the position determined by the measurement unit 15 is a position on the depth image, and thus the display processing unit 16 converts the position into the coordinate system of the two-dimensional image to determine the position of the superimposed mark image.

Figure 4:
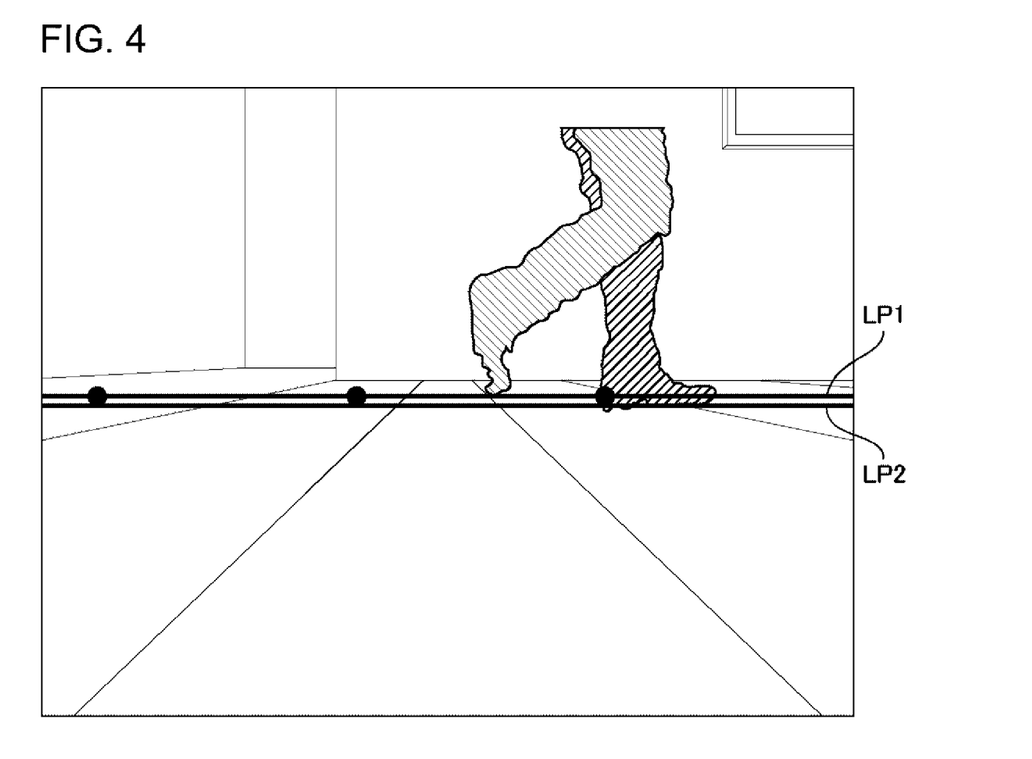
FIG. 4 is a diagram illustrating an example of the display of a two-dimensional image on which a linear image and a mark image are superimposed.

FIG. 4 is a diagram illustrating an example of the display of a two-dimensional image on which a linear image and a mark image are superimposed. In the example of FIG. 4, a mark image is indicated by a circle, and a linear image LP2 parallel to a linear image LP1 is displayed so as to be superimposed, in addition to the linear image LP1 corresponding to the scanning line. The two linear images LP1 and LP2 are displayed, and thus it is possible to cause the test subject to easily recognize the walking passage.

Further, the display processing unit 16 may display information of the walking state measured by the measurement unit 15.

Figure 5:
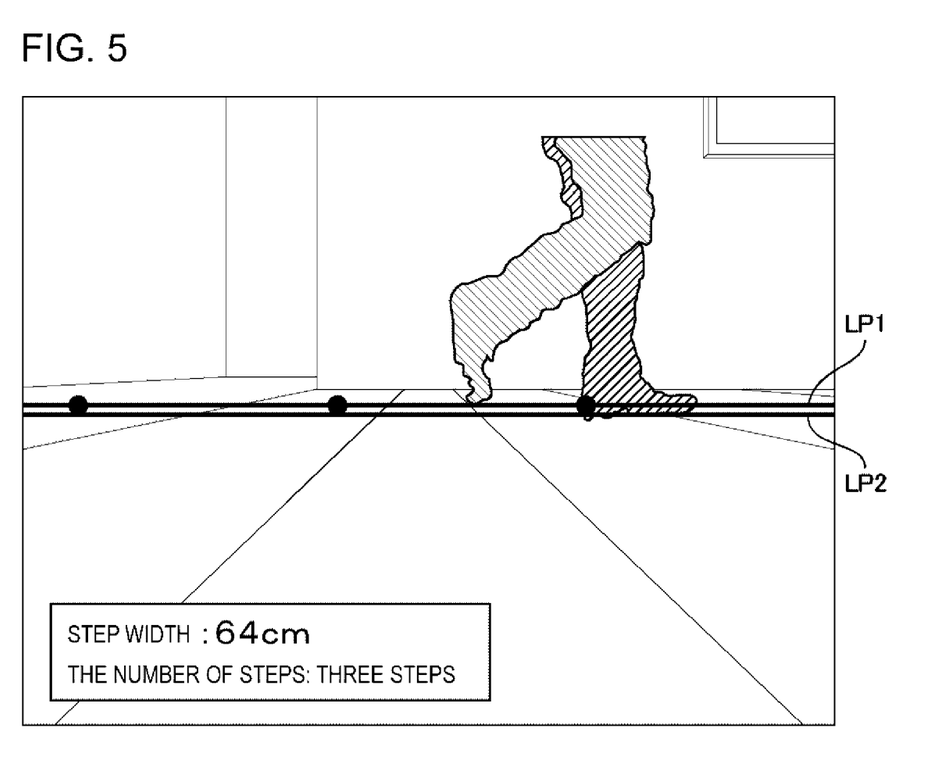
FIG. 5 is a diagram illustrating an example of the display of a two-dimensional image on which information of a measured walking state is further superimposed.

FIG. 5 is a diagram illustrating an example of the display of a two-dimensional image on which information of a measured walking state is further superimposed. In the example of FIG. 5, an actually measured value of a step width and the number of steps which are calculated as the information of the walking state are displayed. The display processing unit 16 may display the information of the walking state in a display region different from the two-dimensional image without superimposing the information on the two-dimensional image.

[Example of Operation/Measurement Method]

Figure 6:
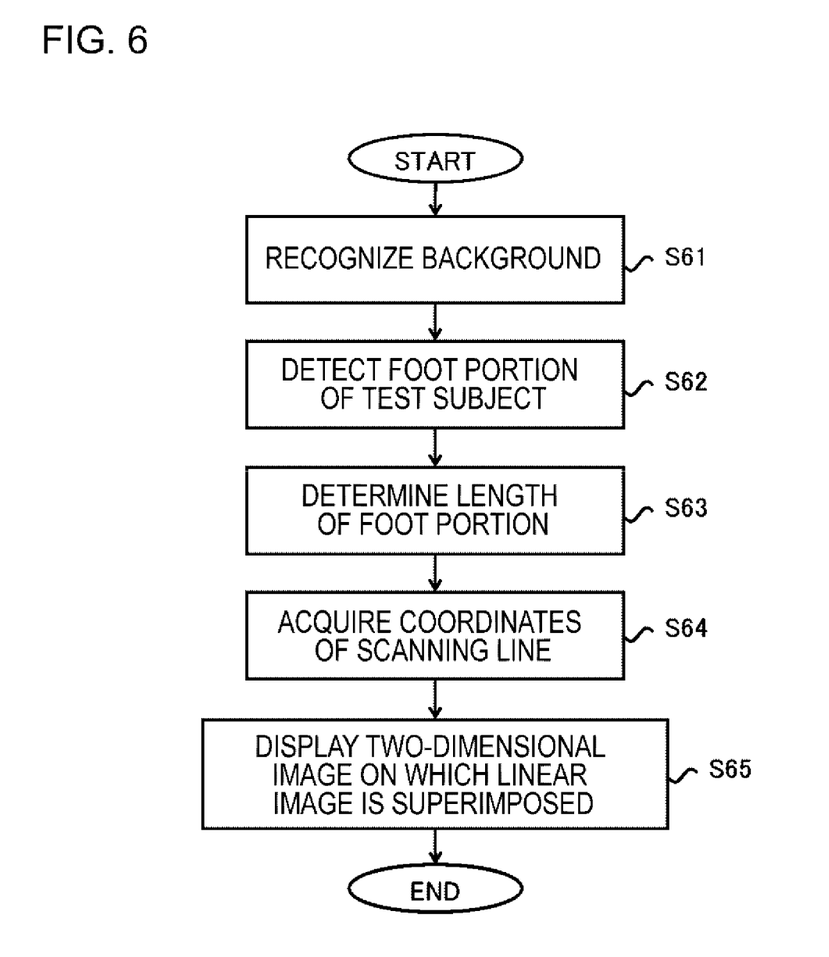
FIG. 6 is a flow chart illustrating an example of the operation of the measurement device at a preparation stage.
Figure 7:
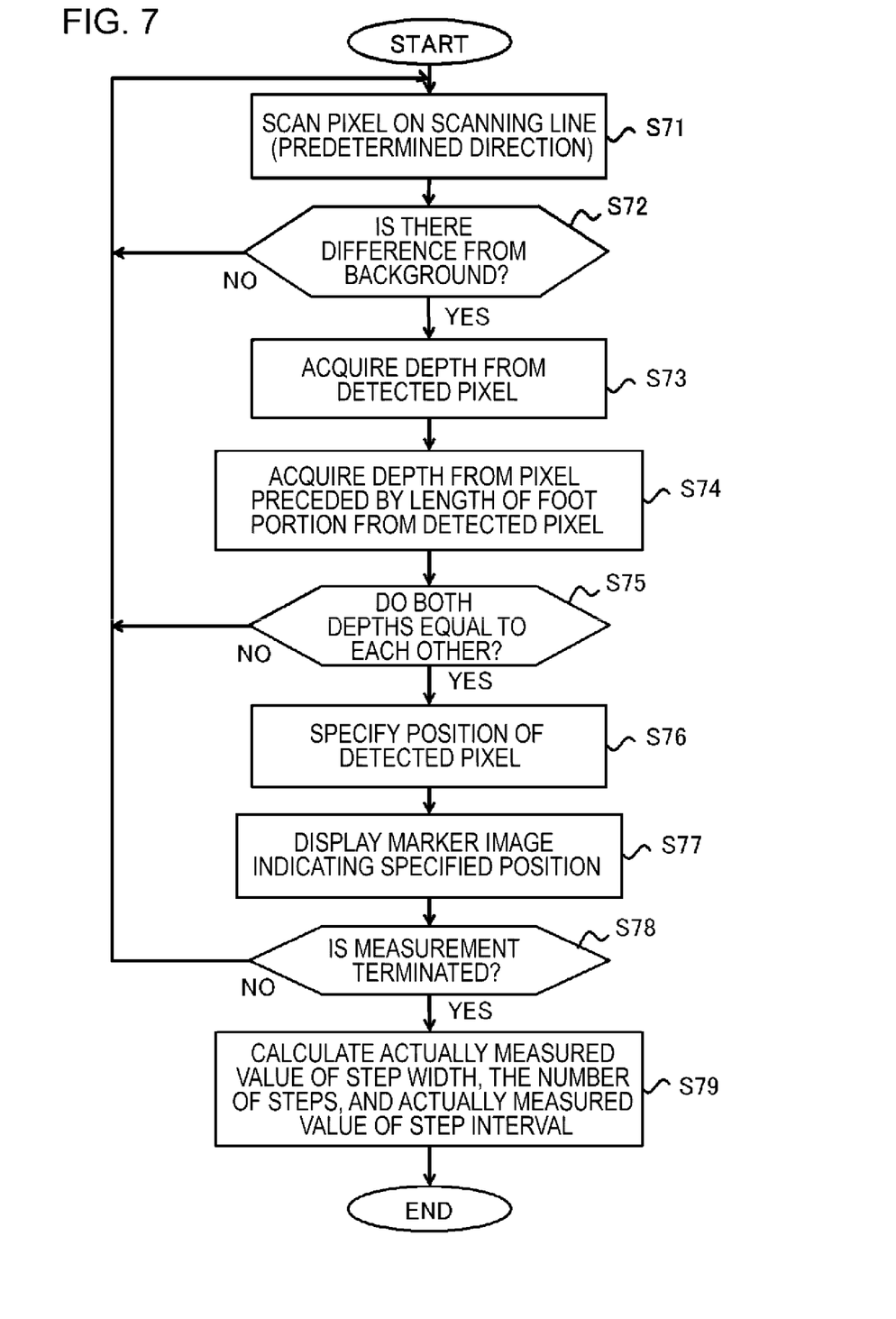
FIG. 7 is a flow chart illustrating an example of the operation of the measurement device at a measurement stage.

Hereinafter, a measurement method according to the first example embodiment will be described with reference to FIGS. 6 and 7. FIGS. 6 and 7 are flow charts illustrating an example of the operation of the measurement device 10 according to the first example embodiment. As illustrated in FIGS. 6 and 7, the measurement method according to the first example embodiment is realized by at least one computer such as the measurement device 10. Processing steps illustrated in FIGS. 6 and 7 are the same as the processing contents of the above-described processing modules included in the measurement device 10, and thus details of the processing steps will be appropriately omitted.

The measurement method according to the first example embodiment is divided into a preparation stage and a measurement stage.

FIG. 6 is a flow chart illustrating an example of the operation of the measurement device 10 at the preparation stage. At the preparation stage illustrated in FIG. 6, the measurement device 10 sequentially displays two-dimensional images acquired from the three-dimensional sensor 7 on the display device 5.

First, the measurement device 10 recognizes a background (S61). At this time, the test subject is required to be outside a sensing region of the three-dimensional sensor 7. The measurement device 10 may display a screen including an instruction sentence of "test subject is required not to stand in front of the three-dimensional sensor 7". The measurement device 10 holds a depth image not including the test subject, which is acquired from the three-dimensional sensor 7, as a background image.

Next, the test subject enters the sensing region of the three-dimensional sensor 7 and stands while the side thereof facing to the three-dimensional sensor 7. At this time, the measurement device 10 may display a screen including an instruction sentence of "test subject is required to stand in front of the three-dimensional sensor 7 to which the side thereof faces" after the holding of the background image is completed. When the measurement device 10 acquires the depth image including the test subject from the three-dimensional sensor 7, the measurement device detects the foot portion of the test subject from a difference between the background image held in (S61) and the acquired depth image (S62). The detected foot portion and a method of detecting the foot portion from the depth image are as described above (detection unit 12).

At this time, the measurement device 10 may color a region indicating the test subject in the displayed two-dimensional image. For example, the measurement device 10 determines the region of the test subject from the depth image, determines a region indicating the test subject within the two-dimensional image on the basis of the determined region, and colors the determined region on the basis of depth information of the test subject.

Subsequently, the measurement device 10 determines the length of the foot portion which is detected in (S62) (S63). The length determined here may be a length (for example, the number of pixels) within the depth image. A method of determining the length of the foot portion is as described above (determination unit 13).

The measurement device 10 acquires coordinates of the scanning line in the coordinate system of the depth image on the basis of the position of the foot portion which is detected in (S62) (S64). The meaning of "scanning line" and a method of acquiring the coordinates of the scanning line are as described above (setting unit 14). In this example embodiment, as described above, the test subject faces its side to the three-dimensional sensor 7, and thus the scanning line is set in the horizontal direction of the depth image.

The measurement device 10 converts the coordinates acquired in (S64) into the coordinate system of the two-dimensional image to superimpose a linear image corresponding to the scanning line on the two-dimensional image and display an image in which the linear image is superimposed on the two-dimensional image (S65). A method of superimposing the linear image with respect to the two-dimensional image is as described above (display processing unit 16). Another linear image parallel to a linear image which is set at the same position as the scanning line may be further superimposed on the two-dimensional image, in addition to the linear image. When such a preparation stage is terminated, the operation proceeds to the subsequent measurement stage.

In this example embodiment, the test subject once departs from the sensing region three-dimensional sensor 7 after the preparation stage is terminated. When the operation proceeds to the measurement stage, the test subject walks along the linear image while viewing the display of the two-dimensional image on which the linear image is superimposed, and passes through the sensing region three-dimensional sensor 7. In a case where the test subject stands at the end of the sensing region of three-dimensional sensor 7 at the preparation stage, the test subject may walk toward the opposite end of the sensing region from the position without departing from the sensing region.

FIG. 7 is a flow chart illustrating an example of the operation of the measurement device 10 at the measurement stage. The measurement device 10 performs the following operation on the two-dimensional image and depth image which are acquired at a certain cycle from the three-dimensional sensor 7.

The measurement device 10 scans a pixel on the coordinates of the scanning line in the acquired depth image in a predetermined direction (S81).

The measurement device 10 detects a pixel having a difference in a pixel value between the pixel on the scanning line in the acquired depth image and a pixel at the corresponding position in the background image held in (S61) illustrated in FIG. 6 (S72). In a case where no difference is detected (S72; NO), the measurement device 10 performs (S71) and the subsequent steps on a depth image to be newly acquired.

In a case where difference is detected (S72; YES), the measurement device 10 acquires a depth (pixel value) from the pixel (referred to as a detected pixel) in which the difference is detected (S73).

Further, the measurement device 10 acquires a depth (pixel value) from the pixel on the scanning line ahead of the detected pixel by an extent of the length of the foot portion which is determined in (S63) illustrated in FIG. 6 (S74).

The measurement device 10 determines whether or not the depth acquired in (S73) and the depth acquired in (S74) equal to each other (S75). Here, the wording "two depths equal to each other" may include not only a case where both the depths are completely equivalent to each other but also a case where both the depths approximate to each other within a predetermined error. In a case where both the depths do not equal to each other (S75; NO), the measurement device 10 performs (S71) and the subsequent steps on a depth image to be newly acquired. The case where both the depths do not equal to each other (S75; NO) is equivalent to a state where the sole of the foot of the test subject is not grounded to the walking surface.

In a case where both the depths equal to each other (S75; YES), the measurement device 10 determines the position of the detected pixel (S76). The determined position indicates a position within the depth image.

The measurement device 10 displays an image in which a mark image indicating the position determined in (S76) is superimposed on the two-dimensional image, together with the linear image superimposed in (S65) illustrated in FIG. 6. At this time, the measurement device 10 converts the position within the depth image which is determined in (S76) into the coordinate system of the two-dimensional image to determine the position of the superimposed mark image.

The measurement device 10 repeatedly performs such a processing step on depth images that are cyclically acquired, until the measurement is terminated (S78; NO). The termination of measurement may be automatically determined in a case where the determination of the position in (S76) is not performed for a predetermined time or longer. In addition, the termination of measurement may be determined on the basis of user operation information obtained from the input device 6.

When the measurement is terminated (S78; YES), the measurement device 10 calculates at least one or more of an actually measured value of a step width, the number of steps, and an actually measured value of a step interval on the basis of the plurality of positions determined in (S76) (S79). A method of calculating the actually measured value of the step width, the number of steps, and the actually measured value of the step interval is as described above (measurement unit 15).

The measurement device 10 can sequentially perform the processing steps illustrated in FIG. 7 whenever a two-dimensional image frame and a depth image (distance image) frame are acquired from the three-dimensional sensor 7. The processing steps illustrated in FIG. 7 may be performed at intervals longer than a cycle for acquiring the frames. The order of execution of the processing steps in the measurement method of this example embodiment is not limited to the examples illustrated in FIGS. 6 and 7. The order of execution of the processing steps can be changed within a range as long as the change does not affect the content.

According to the examples of the operation illustrated in FIGS. 6 and 7, it is possible to measure the walking state of the test subject by using only the depth image. However, the measurement method according to the first example embodiment may additionally use a position indicated by skeleton data (framework data) in addition to the depth image. For example, (S62) in FIG. 6 may include estimating the position of the foot portion of the test subject within the depth image on the basis of the position indicated by the skeleton data, and detecting the foot portion of the test subject in accordance with the distribution of depths in the vicinity of the position.

Advantageous Effects of First Example Embodiment

As described above, in the first example embodiment, the position of a predetermined location within the foot portion in a state where the sole of the foot of the test subject is grounded to the walking surface is determined using the depth of the coordinates of the scanning line acquired at the preparation stage, and the walking state of the test subject is measured using the determined position. In this manner, in the first example embodiment, the walking state of the test subject is measured using the depth image obtained from the three-dimensional sensor 7, and thus it is possible to measure the walking state with a high level of accuracy as compared with measurement based on the position of a framework obtained from skeleton data. This is because a predetermined location, such as the heel, the toe, or the center position of the foot portion, within the foot portion is fixedly determined by analyzing the depth image, and the walking state is measured on the basis of the position of the predetermined location which is fixedly determined.

Further, in the first example embodiment, the position of the predetermined location within the foot portion in the state where the sole of the foot of the test subject is grounded to the walking surface is determined by performing scanning with only a depth on the scanning line, and thus it is possible to increase the speed of the processing as compared to a case where all of the depths shown in the depth image are confirmed.

In addition, in the first example embodiment, the state where the sole of the foot of the test subject is grounded to the walking surface is detected by determining the position of a certain portion of the foot portion and determining whether or not the depth of the determined position of the portion and the depth of a position ahead of the determined position of the portion by the length of the foot portion which is determined at the preparation stage. Thereby, two depths of the position at which a difference from a background is detected and the position ahead of the pixel by the length of the foot portion, among the depths on the scanning line, may be confirmed, and thus it is possible to increase the speed of the processing. Further, the state where the sole of the foot of the test subject is grounded to the walking surface is detected by the determination regarding whether or not the two depths are the same as each other, and thus it is possible to appropriately determine the position of the predetermined location within the foot portion and to accurately detect a single step even when both foots overlap each other.

Modification Example

The measurement device 10 may store a measured walking state in the memory 2 of the measurement device 10 without displaying the walking state. In addition, the measurement device 10 may transmit the measured walking state to another computer and may store the transmitted walking state in a portable storage medium.

In addition, the measurement device 10 may determine whether or not the test subject faces its side to the three-dimensional sensor 7 and may output a display for instructing the test subject face its side to the three-dimensional sensor in a case where the test subject does not face its side to the three-dimensional sensor. In this case, for example, the measurement device 10 causes the test subject to input the length (measured size of the foot) of the foot portion by using the input device 6, and compares the input measured size of the foot and the measured size of the foot estimated from the length of the foot portion which is determined by the determination unit 13. The measurement device 10 can determine that the side the test subject does not face its side to the three-dimensional sensor in a case where both the measured sizes are different from each other over a predetermined error range. A method of calculating the measured size of the foot from the length of the foot portion which is determined by the determination unit 13 is the same as the method of calculating an actually measured value of a step width.

In addition, coordinates of the scanning line in the depth image may be determined in advance. In this case, the measurement device 10 (measurement unit 15) holds the coordinates of the scanning line in advance, and measures a walking state of the test subject by using the held coordinates. Therefore, in this case, the setting unit 14 becomes unnecessary.

Second Example Embodiment

Hereinafter, a measurement device and a measurement method according to a second example embodiment will be described with reference to FIGS. 8 and 9. In addition, the second example embodiment may relate to a program for causing at least one computer to execute the measurement method, or may relate to a storage medium readable by the at least one computer having the program recorded thereon.

Figure 8:
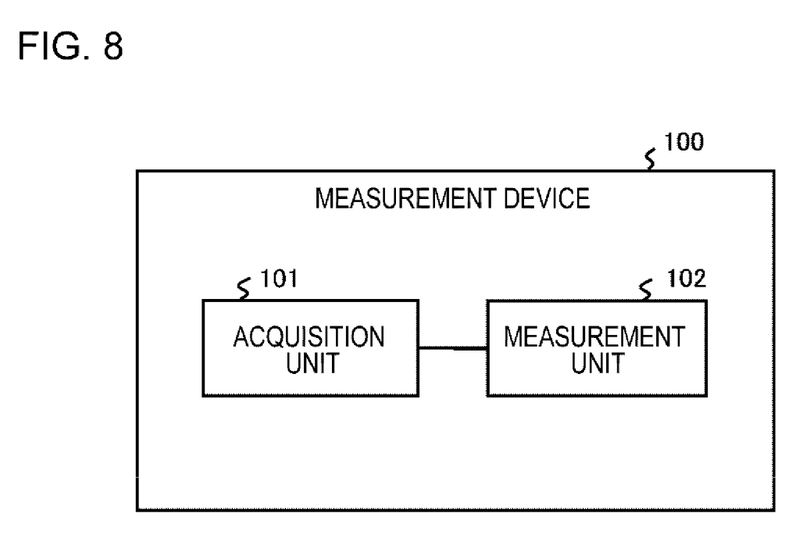
FIG. 8 is a schematic diagram illustrating an example of a processing configuration of a measurement device according to a second example embodiment.

FIG. 8 is a schematic diagram illustrating an example of a processing configuration of the measurement device according to the second example embodiment. As illustrated in FIG. 8, a measurement device 100 includes an acquisition unit 101 and a measurement unit 102. The measurement device 100 illustrated in FIG. 8 has the same hardware configuration as that of, for example, the above-described measurement device 10 illustrated in FIG. 1, and the above-described processing modules are realized by the program being processed similar to the measurement device 10. However, a three-dimensional sensor 7, a display device 5, and an input device 6 may not be connected to the measurement device 100.

The acquisition unit 101 acquires depth information indicating a depth for each two-dimensional position. A specific example of the depth information is the above-described depth image frame. However, the depth information may be shown in any format as long as the depth information is information indicating a depth for each two-dimensional position. The acquisition unit 101 may acquire the depth information from a depth sensor connected to the measurement device 100 or the three-dimensional sensor 7, or may acquire depth information recorded from another computer or a portable storage medium.

The measurement unit 102 measures a walking state of a test subject by using the depth information acquired by the acquisition unit 101. For example, the measurement unit 102 has a problem in a processing speed as compared to the above-described example embodiment, but can measure the walking state by the following method. The measurement unit 102 determines a predetermined location within a foot portion of the test subject from the depth information, and detects a state where the predetermined location is grounded to a walking surface. The measurement unit 102 can determine a region of the test subject on the basis of a difference from a background image, and can determine the predetermined location within the foot portion from the region of the test subject. Further, the measurement unit 102 can detect the state where the predetermined location of the foot portion is grounded to the walking surface from the form and direction (horizontal) of the foot portion. The measurement unit 102 determines the position of the predetermined location when the state is detected. In this manner, the measurement unit 102 can measure the walking state using the depth information not only by the method according to the above-described example embodiment but also by various other methods.

The walking state measured by the measurement unit 102 may be an actually measured value of a step width, the number of steps, or both of them, similar to the above-described example embodiment, or may be another index value such as fluctuations in a step speed, a step width, and the like. The walking state may be any index value as long as the index value is an index value calculated on the basis of information determined with respect to the walking of the test subject by using depth information.

Figure 9:
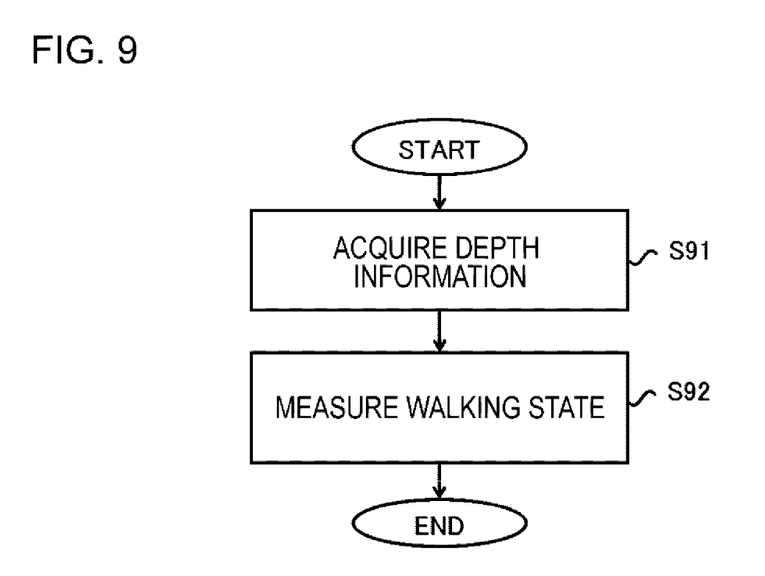
FIG. 9 is a flow chart illustrating an example of the operation of the measurement device according to the second example embodiment.

FIG. 9 is a flow chart illustrating an example of the operation of the measurement device 100 according to the second example embodiment. As illustrated in FIG. 9, the measurement method according to the second example embodiment is performed by at least one computer such as the measurement device 100. For example, steps illustrated in the drawing are performed by processing modules included in the measurement device 100.

The measurement method according to this example embodiment includes acquiring depth information indicating a depth for each two-dimensional position (S91), and measuring a walking state of the test subject by using the depth information acquired in (S91) (S92). Contents of (S91) are as described with regard to the acquisition unit 101, and contents of (S92) are as described with regard to the measurement unit 102.

The measurement device 100 stores the measured walking state. The measurement device 100 can also display the measured walking state, may transmit the measured walking state to another computer, and may store the measured walking state in the portable storage medium.

According to the second example embodiment, the walking state of the test subject is measured using the depth information, and thus it is possible to measure the walking state with a higher level of accuracy as compared to measurement based on the position of a framework obtained as skeleton data, similar to the above-described example embodiment.

The above-described example embodiments and modification example can be combined with each other in a range in which the contents thereof do not conflict with each other.

A portion or all of the above-described example embodiments and modification example may be determined as follows. However, the above-described contents are not limited to the following description.

1. A measurement device including:
a first acquisition unit that acquires depth information indicating a depth for each two-dimensional position; and
a measurement unit that measures a walking state of a test subject by using the depth information.

2. The measurement device according to 1, further including:
a second acquisition unit that acquires a two-dimensional image; and
a display processing unit that displays an image in which a linear image is superimposed on the acquired two-dimensional image,
wherein the measurement unit measures the walking state of the test subject by using depth information on a scanning line corresponding to the linear image.

3. The measurement device according to 2,
wherein the measurement unit determines a position of a predetermined location within a foot portion in a state where a sole of a foot of the test subject is grounded to a walking surface, by using the depth information on the scanning line, and measures the walking state of the test subject by using the determined position, and wherein the display processing unit displays an image in which a mark image indicating the determined position is superimposed on the acquired two-dimensional image together with the linear image.

4. The measurement device according to 3, further including:

a detection unit that detects the foot portion of the test subject from the acquired depth information; and a determination unit that determines a length of the detected foot portion, wherein the measurement unit performs scanning with depth information along the scanning line in a predetermined direction to determine a position of a certain portion of the foot portion grounded to the walking surface, and determines whether or not a depth of the determined position of the portion is the same as a depth of a position ahead of the determined position of the portion by the determined length of the foot portion of the test subject to detect the state where the sole of the foot of the test subject is grounded to the walking surface.

5. The measurement device according to 3 or 4, wherein the measurement unit calculates any one or more of an actually measured value of a step width, the number of steps, and a step interval on the basis of the plurality of positions determined.

6. The measurement device according to any one of 2 to 5, further including:

a detection unit that detects the foot portion of the test subject from the acquired depth information; and a setting unit that acquires coordinates of the scanning line in a two-dimensional coordinate system indicated by the depth information, on the basis of a position of the detected foot portion, wherein the display processing unit converts the acquired coordinates of the scanning line into a coordinate system of the two-dimensional image to display the image in which the linear image is superimposed on the two-dimensional image.

7. A measurement method performed by at least one computer, the measurement method including:

acquiring depth information indicating a depth for each two-dimensional position; and measuring a walking state of a test subject by using the depth information.

8. The measurement method according to 7, further including:

acquiring a two-dimensional image; and displaying an image in which a linear image is superimposed on the acquired two-dimensional image, wherein the measuring includes measuring the walking state of the test subject by using depth information on a scanning line corresponding to the linear image.

9. The measurement method according to 8, wherein the measuring includes determining a position of a predetermined location within a foot portion in a state where a sole of a foot of the test subject is grounded to a walking surface, by using the depth information on the scanning line, and measuring the walking state of the test subject by using the determined position, and wherein the displaying includes displaying an image in which a mark image indicating the determined position is superimposed on the acquired two-dimensional image together with the linear image.

10. The measurement method according to 9, further including:

detecting the foot portion of the test subject from the acquired depth information; and determining a length of the detected foot portion, wherein the determining of the position includes performing scanning with depth information along the scanning line in a predetermined direction to determine a position of a certain portion of the foot portion grounded to the walking surface, and determining whether or not a depth of the determined position of the portion is the same as a depth of a position ahead of the determined position of the portion by the determined length of the foot portion of the test subject to detect the state where the sole of the foot of the test subject is grounded to the walking surface.

11. The measurement method according to 9 or 10, wherein the measuring including calculating any one or more of an actually measured value of a step width, the number of steps, and a step interval on the basis of the plurality of positions determined.

12. The measurement method according to any one of 8 to 11, further including:

detecting the foot portion of the test subject from the acquired depth information; and acquiring coordinates of the scanning line in a two-dimensional coordinate system indicated by the depth information, on the basis of a position of the detected foot portion, wherein the displaying includes converting the acquired coordinates of the scanning line into a coordinate system of the two-dimensional image to display the image in which the linear image is superimposed on the two-dimensional image.

13. A program causing at least one computer to execute the measurement method according to one of 7 to 12.

The invention claimed is:

1. A measurement device comprising:

a memory storing one or more instructions; and a processor configured to execute the one or more instructions to:

acquire a depth image including depth information generated by a sensor, the depth information indicating a depth from the sensor to each of positions in a sensing area of the sensor by a value of each pixel of the depth image;

measure a walking state of a test subject by using the depth information;

acquire a two-dimensional image of an area corresponding to the sensing area; and display an image in which a linear image showing a walking passage for measurement is superimposed on the two-dimensional image, wherein the processor measures the walking state of the test subject by using, among the depth information on all pixels of the depth image, depth information on a scanning line including a sequence of pixels of the depth image corresponding to a sequence of pixels of the two-dimensional image where the linear image is positioned.

2. The measurement device according to claim 1, wherein the processor is further configured to determine a position of a predetermined location within a foot portion in a state where a sole of a foot of the test subject is grounded to a walking surface, by using the depth information on the scanning line, and measures the walking state of the test subject by using the position of the predetermined location, and wherein the processor is further configured to display the image in which a mark image indicating the position of the predetermined location is superimposed on the two-dimensional image together with the linear image.

3. The measurement device according to claim 2, wherein the processor is further configured to:

detect the foot portion of the test subject from the depth information; and determine a length of the foot portion, wherein the processor is further configured to perform scanning with depth information along the scanning line in a predetermined direction to determine a first pixel whose depth information indicates a depth different from that in a background region of the depth image, and determines whether or not a depth of the first pixel is the same as a depth of a second pixel ahead of the first pixel by the length of the foot portion of the test subject to detect the state where the sole of the foot of the test subject is grounded to the walking surface.

4. The measurement device according to claim 2, wherein the processor is further configured to:

acquire a plurality of depth image and a plurality of two-dimensional images;

determine the position of the predetermined location for each of the plurality of depth images to acquire a plurality of positions of the predetermined location; and calculate, based on the plurality of positions, any one or more of a value of a step width, a number of steps, and a step interval.

5. The measurement device according to claim 1, further comprising:

wherein the processor is further configured to detect the foot portion of the test subject from the depth information; and wherein the processor is further configured to acquire, based on a position of the foot portion, coordinates of the scanning line in a two-dimensional coordinate system indicated by the depth information, wherein the processor is further configured to convert the coordinates of the scanning line into a coordinate system of the two-dimensional image to display the image in which the linear image is superimposed on the two-dimensional image.

6. A measurement method performed by at least one computer, the measurement method comprising:

acquiring a depth image including depth information generated by a sensor, the depth information indicating a depth from the sensor to each of positions in a sensing area of the sensor by a value of each pixel of the depth image;

measuring a walking state of a test subject by using the depth information acquiring a two-dimensional image of an area corresponding to the sensing area; and displaying an image in which a linear image showing a walking passage for measurement is superimposed on the two-dimensional image, wherein the walking state of the test subject is measured by using, among the depth information on all pixels of the depth image, depth information on a scanning line including a sequence of pixels of the depth image corresponding to a sequence of pixels of the two-dimensional image where the linear image is positioned.

7. A non-transitory computer-readable medium storing a program causing at least one computer to execute the measurement method according to claim 6.

\* \* \* \* \*